US00PP09006P

United States Patent [19]

Bloom

[11] Patent Number: Plant 9,006

[45] Date of Patent: Dec. 6, 1994

[54] *GERANIUM SANGUINEUM* 'ALAN BLOOM'

[75] Inventor: Alan H. V. Bloom, Bressingham, England

[73] Assignee: Blooms of Bressingham Ltd., Bressingham, England

[21] Appl. No.: 145,609

[22] Filed: Nov. 4, 1993

[51] Int. Cl.[5] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Keith D. Gehr

[57] ABSTRACT

A new variety of Geranium which bears prolific pink flowers beginning in June and continues to flower into September. The plant has semi-evergreen foliage and is winter hardy. It has a low growing spreading habit and is ideal for use in borders and containers.

2 Drawing Sheets

The present invention relates to a new and distinct variety of a hardy perennial herbaceous plant of the genus Geranium, a member of the Geraniaceae family.

This new variety of Geranium was discovered as an open pollinated seedling of *Geranium sanguineum* 'Shepherds Warning'. It has been reproduced by root cuttings at Bloom of Bressingham Ltd. nursery. Bressingham, Diss, Norfolk, England. Each of the progeny of the first and succeeding generations exhibits characteristics identical to the mother plant. This particular variety has pink blossoms and is characterized by prolific flowering, excellent vigor, and the same flowering habit as the species. *Geranium sanguineum* 'Alan Bloom' is quite distinct from other pink flowering geranium varieties. It forms a low spreading clump which flowers for many months, often starting as early as June and continuing until September. The deeply cut foliage makes a pleasing backdrop to clusters of bright pink flowers. The plant will thrive in habitats from full sun to partial shade and is generally drought resistant.

The flowers are of classic geranium type and superficially resemble those of *Geranium sanguineum*, the compact form of the 'Bloody Cranesbill', except for color. The variety also has a resemblance to *Geranium sanguineum* 'John Elsley' but is shorter in height and less vigorous, its flowers more pink than magenta.

BRIEF DESCRIPTION OF THE PHOTOGRAPHS

DETAILED PLANT DESCRIPTION

Figure 1:
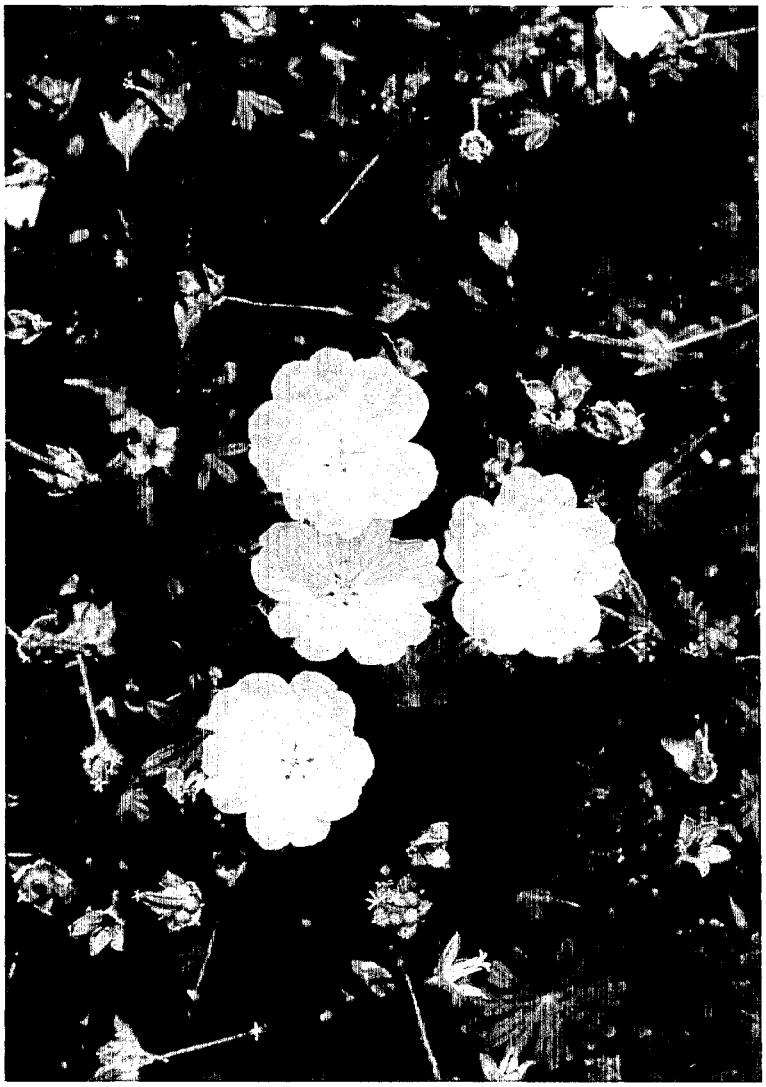
FIG. 1 is a close up view of the plant emphasizing the deeply cut foliage and the profuse blooming habit.
Figure 2:
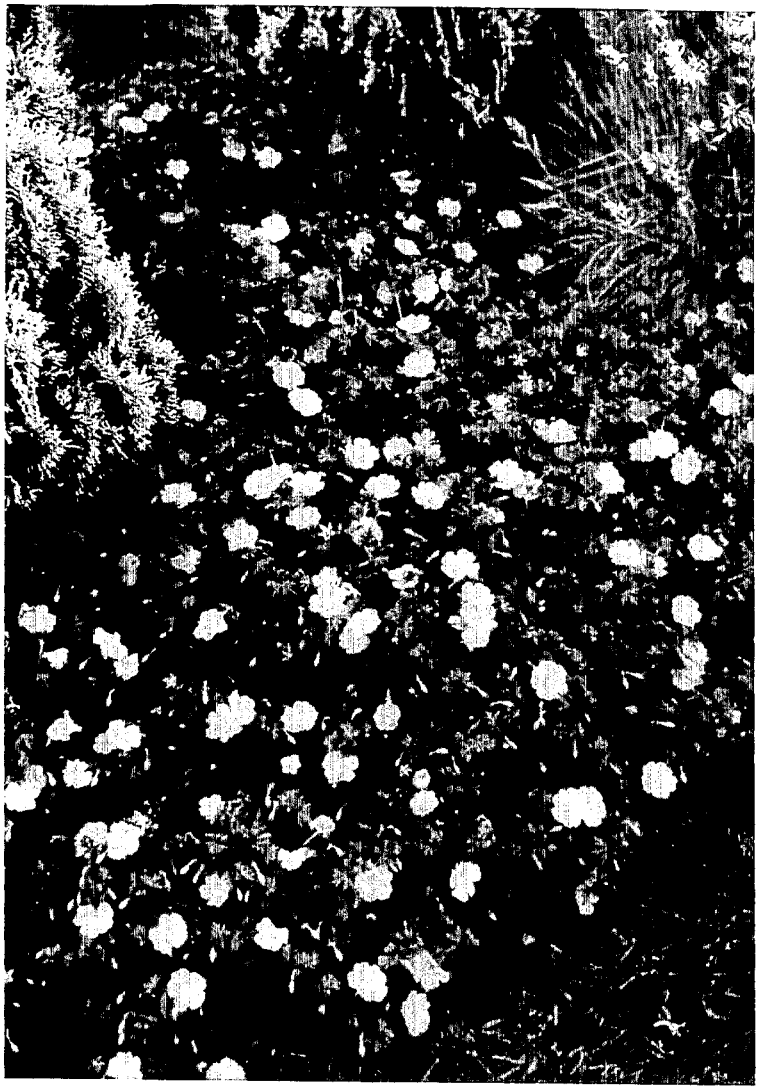
FIG. 2 is a view of the plant growing in a border setting.

The following is a detailed description of the new Geranium variety. All color determinations and comparisons are based on The Royal Horticultural Society Colour Charts.

Origin: Seedling selection.
Parentage: Seed parent was open pollinated *Geranium sanguineum* 'Shepherds Warning'.
Habit: Mounded.
Size: Mature plants are 30 cm in height with a spread of about 40 cm.
Root system: Fleshy.
Habit: Mounded.

Plant vigor: A perennial that shows vigorous and healthy growth throughout Great Britain.
Blooming habit: The large pink flowers are borne on a spreading raceme from a flower stem arising at the base of the plant.
Blooming period: From June continuing into September.
Hardiness: Winter hardy throughout the British Isles. The plant has not been fully tested for maximum summer tolerance above 32° C. (90° F.).
Odor: The herbaceous parts of the plant are characterized by a definite odor. This is most noticable if one brushes against the foliage. Crushing the leaves produces less fragrance. The odor appears to come from the underside of the leaves.
Branching and stems: The stems become decumbent after elongation to the 8 to 15 cm range. Stems arise from a rosette of leaves crowded onto a much abbreviated rooted stem. From the axils of the upper-most leaves arises a group of radiating flowering branches. Each of these begins at an internode which bears a pair of opposite leaves at the top. Beneath the bases of these leaves (in their axils) arises a pair of branches and between these a pair of flowers. This system of forking continues producing a dense canopy of branched foliage. The forking stems carry between 6 and 8 nodes, leaves diminishing in size to become mere bracts with a simplified outline. Stipules are brown and scale-like, attached at the base of the petiole, and arranged as two opposite, in similar manner as the leaves. The plant does not self layer.

Foliage

Arrangement: Petiole arising from base of plant bearing deeply cut, compound leaves.
Type: Semi-evergreen.
Texture: Both upper and lower surfaces hairy.
Length: About 3 cm.
Width: About 4 cm.
Petiole length: 8–15 cm.
Margins: Parted.
Apex: Obtuse.
Base: Sagittate.

Flowers

Petal count: Five of equal size.
Flower shape: Compound.
Flower type: Flat saucer shaped, five separate petals.

Flower size: 3 cm diameter.

Carpels: Small.

Stamens: Small.

Blooming habit: Generally three to five blossoms on a raceme rising from the base of the plant. New flowers form regularly during the blooming period and pinching of spent blooms is not necessary to ensure continued formation of new blooms.

Blooming period: Beginning in June and continuing into September.

Fertility: The plants appear to be self fertile but would be likely be cross pollinated assuming the proximity of other pollen sources. After fertilization there is a rapid growth in the length of the style to form the rostrum. Seeds are dispersed by explosive breakup of the rostrum as it dries out. The seeds are fertile and beds of the variety would be subject to contamination by off type seedlings unless spent blooms are pinched and seed not allowed to set.

Color Characteristics

Foliage: Mature leaves, upper surface RHS Colour Chart Fan 3, Green Group 139A; lower surface Green Group 138B.

Flowers: Upper petal surface, RHS Colour Chart Fan 1, Red Group 55A. Veins are Fan 1, Red Group 53C. Color at petal bases is Fan 1, Red Group 55C.

I claim:

1. A new and distinct variety of Geranium, substantially as shown and described and characterized by prolific flowering, having clusters of pink blossoms on racemes arising from the plant base, excellent vigor and hardiness being semi-evergreen, and a flowering season from June into September, longer than normal for the species.

* * * * *